(12) United States Patent
Moszner et al.

(10) Patent No.: US 6,569,917 B1
(45) Date of Patent: May 27, 2003

(54) DENTAL MATERIALS BASED ON POLYSILOXANES

(75) Inventors: Norbert Moszner, Eschen (LI); Thomas Völkel, Oberreitnau (DE); Sabine Stein, Nenzing (AT); Volkner Rheinberger, Vaduz (LI)

(73) Assignee: Ivoclar AG (LI)

( * ) Notice: Subject to any disclaimer, the term of this patent is extended or adjusted under 35 U.S.C. 154(b) by 0 days.

(21) Appl. No.: 09/488,489

(22) Filed: Jan. 20, 2000

Related U.S. Application Data
(60) Provisional application No. 60/156,507, filed on Sep. 28, 1999.

(30) Foreign Application Priority Data

Jan. 21, 1999 (DE) ......................................... 199 03 177

(51) Int. Cl.$^7$ ................................................. A16F 2/00
(52) U.S. Cl. ....................... 523/115; 523/116; 523/118; 528/26; 524/588
(58) Field of Search ............................ 528/26; 523/109, 523/113–121; 524/588

(56) References Cited

U.S. PATENT DOCUMENTS

| | | | |
|---|---|---|---|
| 5,260,350 A | | 11/1993 | Wright |
| 5,717,125 A | | 2/1998 | Wolter et al. |
| 5,866,630 A | * | 2/1999 | Mitra ........................ 523/118 |

FOREIGN PATENT DOCUMENTS

| | | |
|---|---|---|
| DE | 34 07 087 C3 | 9/1985 |
| DE | 41 25 201 C1 | 7/1991 |
| DE | 41 33 494 C2 | 4/1993 |
| DE | 44 16 857 C1 | 5/1994 |
| DE | 44 16 857 C1 | 6/1995 |
| DE | 196 19 046 A1 | 6/1997 |
| DE | 197 14 320 A1 | 10/1998 |
| EP | 0 230 342 A2 | 7/1987 |

OTHER PUBLICATIONS

Wolter et al., "New Inorganic/Organic Copolymers (ORMCER®S) For Dental Applications," *MRS Proceedings, Reprint, Materials Research Society Symposium Proceedings*, 346 Date unknown.

Wolter et al., "Urethane (Meth) Acrylate Alkoxysilanes, A New Type of Reactive Compounds for the Preparation of Inorganic–Organic Copolymers (ORMOCE®S)," *Polymer & Materials Research Symposium 1993*, Bayreuth, pp. 14–17.

Wolter et al, "Dental Filling Materials (Posterior Composites) Based on Inorganic/Organic Copolymers (ORMOCER®S)," MACRO AKRON '94, 35$^{th}$ IUPAC, International Symposium on Macromolecules, Ohio (1994) (abstract).

Wolter et al., "Neuartige Silanklasse—Werkstoffe für Formköper," *ISC–Tätigkeitsbericht*, pp. 61–72 (1992).

Dictionary, p. 899 Date unknown.

* cited by examiner

*Primary Examiner*—Cephia D. Toomer
(74) *Attorney, Agent, or Firm*—Nixon Peabody LLP

(57) ABSTRACT

The invention relates to dental materials which contain at least one polysiloxane based on one or several silanes according to formula (I)

$$[(W_q-R^6-Z)_p-R^3]_m Y-R^2-SiX_n R^1{}_{3-n} \quad \text{Formula (I)}$$

in which X stands for a halogen atom, a hydroxyl, alkoxy and/or acyloxy group; n is equal to 1 to 3, $R^1$ stands for an alkyl, alkenyl, aryl, alkylaryl, arylalkyl group; $R^2$ stands for an alkylene group; $R^3$ stands for a p-time substituted, straight, branched or cyclic, saturated or unsaturated, aromatic or aliphatic organic radical with 2 to 40 carbon atoms and optionally 1 to 6 heteroatoms; $R^6$ stands for a q-times substituted, straight, branched or cyclic organic radical with 1 to 20 carbon atoms or is absent; p is equal to 1 to 6; q is equal to 1 to 6; Y stands for —$NR^4$—, N or —(C=O)—NH—; m is equal to 2 for Y=N and equal to 1 for Y=—$NR^4$—, or —(C=O)—NH—; $R^4$ stands for an alkyl or aryl group; Z stands for O, S, —(C=O)—O—, —(C=O)—NH—, —O—(C=O)—NH— or is absent; W stands for $CH_2=CR^5$—(C=O)—O—; and $R^5$ stands for a hydrogen atom or an alkyl group and optionally one or several further hydrolytically condensable compounds of silicon, aluminium, zirconium, titanium, boron, tin, vanadium and/or phosphorus.

13 Claims, No Drawings

DENTAL MATERIALS BASED ON POLYSILOXANES

This application claims benefit of No. 60/156,507, filed Sep. 28, 1999.

The invention relates to dental materials based on methacrylate-modified polysiloxanes capable of polymerization.

Dental materials based on silanes capable of polymerization are known. DE 36 10 804 A1 discloses dental resin compositions which contain siloxane polymers, monomers which are co-polymerizable with the siloxane polymer, and a polymerization catalyst. The dental resin compositions are said to have an improved compressive strength, abrasion resistance and flexural strength after polymerization.

DE 34 07 087 A1 and WO 92/16183 relate to the use of compounds based on organically modified silicic acid polycondensates for coating teeth and tooth-replacement parts. The cured coats are said to be resistant to the build-up of plaque.

Dental resin compositions based on polymerizable polysiloxanes are known from DE 41 33 494, which are manufactured by hydrolytic condensation of one or several silanes of which at least one is substituted by a 1,4,6-trioxaspiro-[4,4]-nonane radical or a (meth)acrylate group, the latter preferably containing a thioether function. The dental resin compositions are said to show only a small change in volume during curing, however silanes with orthoester groups are difficult of access and less storage-stable whereas thioether groups are sensitive to oxidation.

DE 196 19 046 discloses low-shrinkage polymerizable compounds based on mercapto- or norboronnene silanes and a reaction partner for the en-thiolpolymerization. The curing of these compositions is accompanied by low polymerization shrinkage and results in products with high mechanical strength which however also contain thioether groups sensitive to oxidation.

The object of the invention is the provision of dental materials based on polysiloxanes which can be covalently incorporated in organic-inorganic composite materials and do not contain spiro- or thioether groups.

The object is achieved by dental materials which contain at least one polysiloxane based on one or several silanes according to the formula (I)

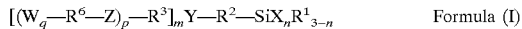

$$[(W_q\text{—}R^6\text{—}Z)_p\text{—}R^3]_m\text{Y—}R^2\text{—}SiX_nR^1_{3-n}$$ Formula (I)

in which

| | |
|---|---|
| X | stands for a halogen atom, a hydroxyl, alkoxy and/or acyloxy group; |
| n | is equal to 1 to 3; |
| $R^1$ | stands for an alkyl, alkenyl, aryl, alkylaryl, arylalkyl group; |
| $R^2$ | stands for an alkylene group; |
| $R^3$ | stands for a p-times substituted, straight, branched or cyclic, saturated or unsaturated, aromatic or aliphatic organic radical with 2 to 40 carbon atoms and optionally 1 to 6 heteroatoms; |
| $R^6$ | stands for a q-times substituted, straight, branched or cyclic organic radical with 1 to 20 carbon atoms or is absent; |
| p | is equal to 1 to 6; |
| q | is equal to 1 to 6; |
| y | stands for —$NR^4$—, N or —(C=O)—NH—; |
| m | is equal to 2 for Y = N and equal to 1 for Y = —$NR^4$— or —(C=O)—NH—; |
| $R^4$ | stands for an alkyl or aryl group; |
| Z | stands for O, S, —(C=O)—O—, —(C=O)—NH—, —O—(C=O)—NH— or is absent; |
| W | stands for $CH_2$=$CR^5$—(C=O)—O—; and |
| $R^5$ | stands for a hydrogen atom or an alkyl group. |

Suitable heteroatoms are phosphorus and preferably oxygen.

In the whole description as well as the claims, alkyl, acyloxy, alkoxy, alkenyl groups and alkylene groups are understood to mean radicals which preferably contain 1 to 25 carbon atoms, particularly preferably 1 to 10 carbon atoms and quite particularly preferably 1 to 4 carbon atoms, and optionally carry one or several subsituents such as for example halogen atoms, nitro groups or alkyloxy radicals. Aryl means radicals, groups or substituents which preferably have 6 to 10 carbon atoms and can be substituted as stated above. The above definitions are also valid for compound groups such as for example alkyl aryl and aryl alkyl groups. An alkyl aryl group thus describes for example an aryl group defined as above which is substituted by an alkyl group as defined above.

The alkyl, acyloxy, alkoxy, alkenyl groups and alkylene groups can be straight-chained, branched or cyclic.

Preferred definitions, which can be chosen independently from each other, for the individual variables, are:

| | |
|---|---|
| X | = a methoxy and/or ethoxy group; |
| n | = 2 or 3; |
| $R^1$ | = a $C_1$ to $C_3$ alkyl group, in particular a methyl group; |
| $R^2$ | = a $C_1$ to $C_4$ alkylene group; |
| $R^3$ | = a p-times substituted, straight, branched or cyclic, saturated or unsaturated, aromatic or aliphatic organic radical with 2 to 10 carbon atoms and optionally a heteroatom, preferably an oxygen atom, particularly preferably a $C_1$ to $C_4$ alkenylene radical or a monocyclic radical with 4 to 10, in particular 5 to 8 carbon atoms; |
| $R^6$ | = a q-times substituted, straight, branched or cyclic organic radical with 1 to 4 carbon atoms, particularly preferably a $C_1$ to $C_3$ alkylene radical; |
| p | = 1 or 2, in particular 1; |
| q | = 1 or 2; |
| Y | = N or —(C=O)—NH—; |
| Z | = —(C=O)—O—; and/or |
| $R^5$ | = a hydrogen atom or a methyl group. |

Concrete examples of particularly preferred silanes according to formula (I) are:

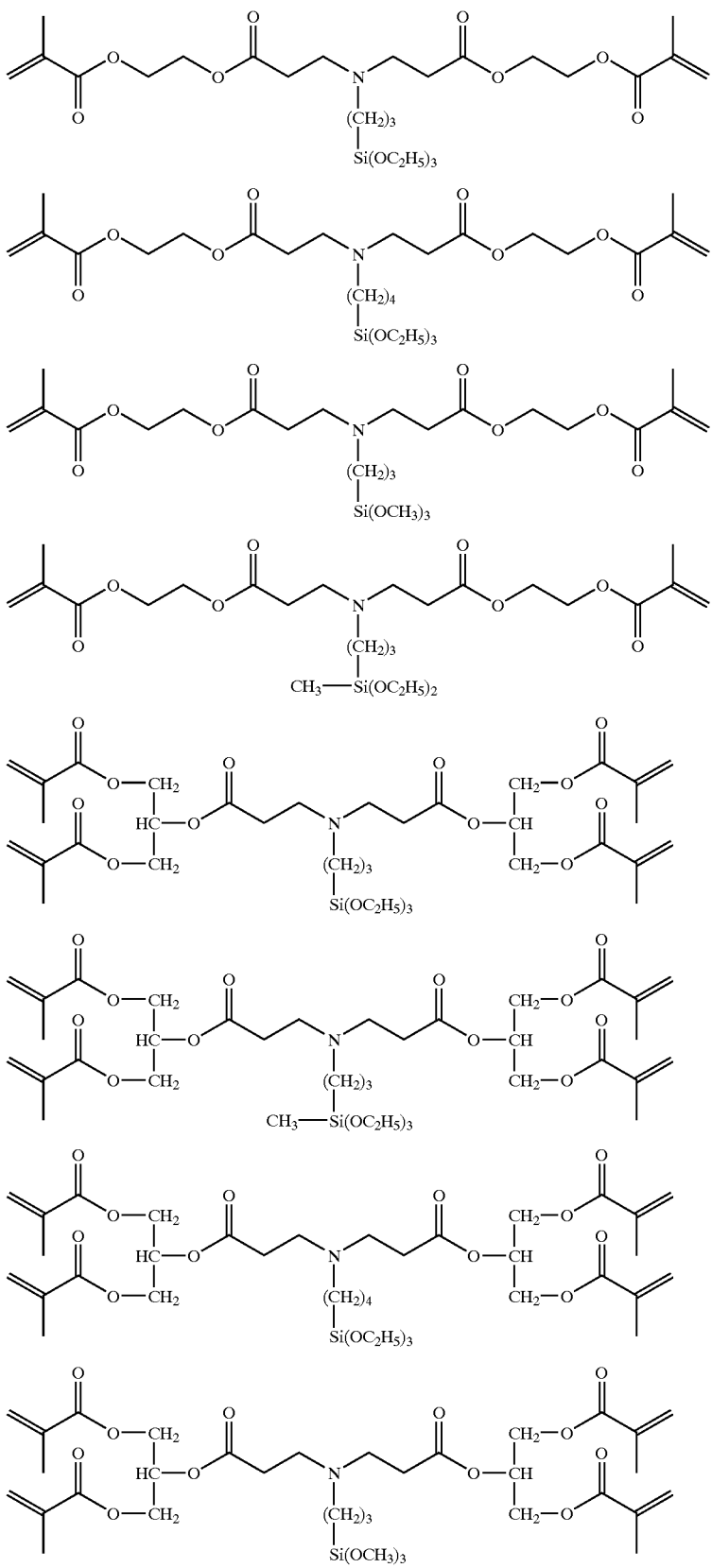

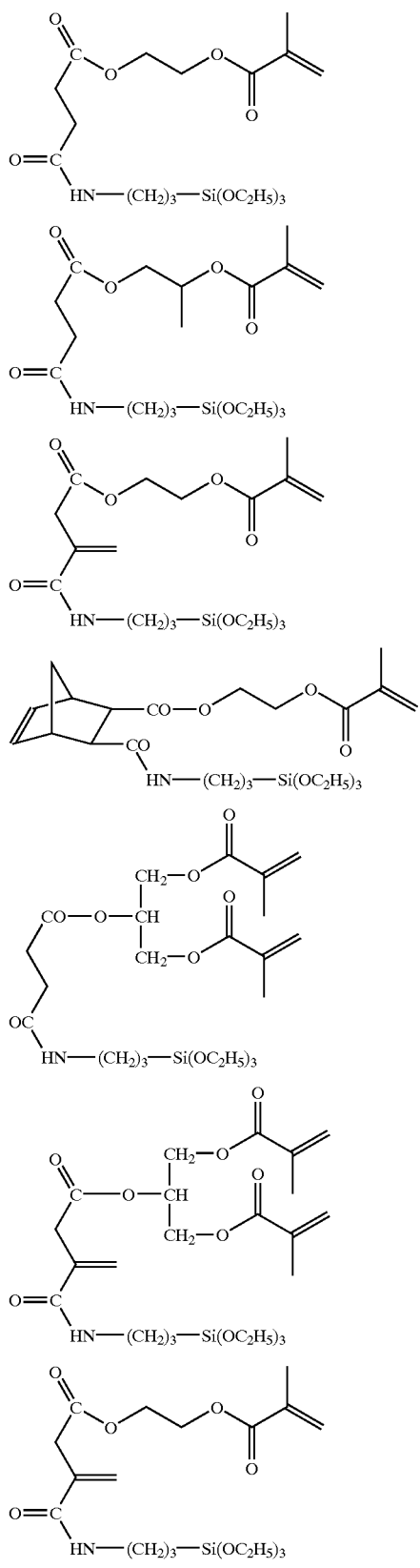
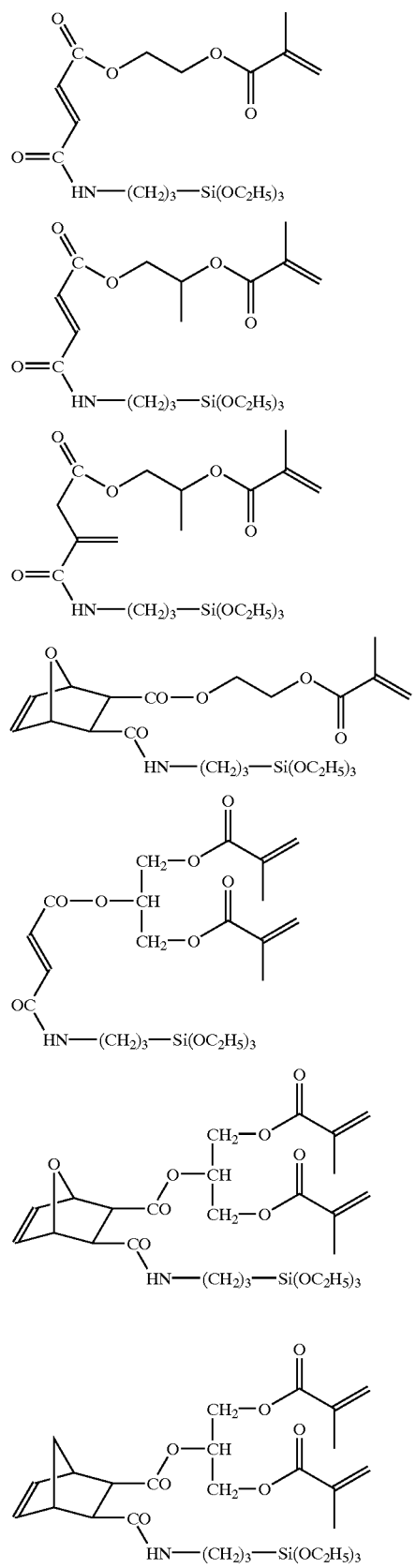

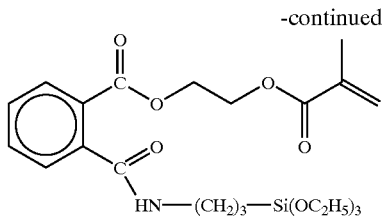

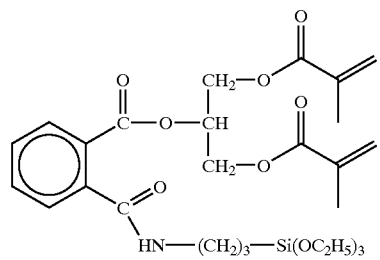

The silanes of formula (I) are accessible via addition and condensation reactions known per se, the number of hydrolyzable groups, groups capable of polymerization, and further functional groups being able to be varied by the appropriate selection of educts.

Silanes in which Y has the meaning —NR$^4$— or N are for example accessible by addition of an aminosilane compound to an m-times unsaturated group R$^3$:

$$(W-Z)_{\overline{p}}(R^3\text{-}2mH) \quad + \quad H_mY-R^2-SiX_nR^1_{3-n}$$

$$\downarrow$$

$$[(W-Z)_{\overline{p}}-R^3]_mY-R^2-SiX_nR^1_{3-n}$$

Thus e.g., bis[2-(2-methacryloyloxyethoxycarbonyl)-ethyl]-(3-triethoxysilylpropyl)amine is obtained by reacting 3-amino-propyltriethoxysilane with 2-acryloyloxyethylmethacrylate:

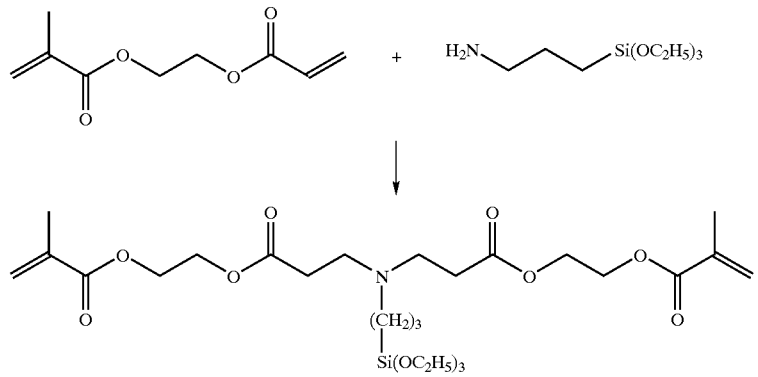

Silanes in which Y is equal to —(C═O)—NH— are accessible for example by reacting an isocyanatosilane with a carboxylic acid which contains p radicals W capable of polymerization:

$$(W-Z)_{\overline{p}}-R^3-COOH \quad + \quad OCN-R^2-SiX_nR^1_{3-n}$$

$$\downarrow -CO_2$$

$$(W-Z)_{\overline{p}}-R^3-Y-R^2-SiX_nR^1_{3-n}$$

$$(Y = CO-NH)$$

The reaction of 3-isocyanatopropyltriethoxysilane with 2-methacryloyloxyethyl-hydrogen-succinate results in e.g. 2-methacryloxyethyl-3-[(3-triethoxysilyl) propylaminocarbonyl]propionate:

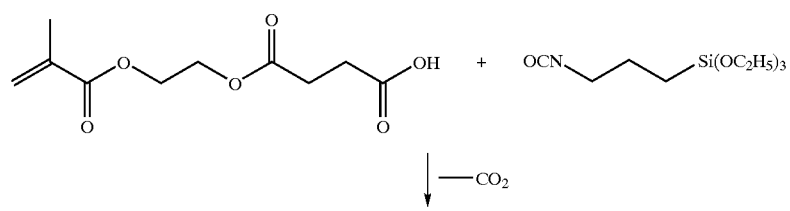

$$\downarrow -CO_2$$

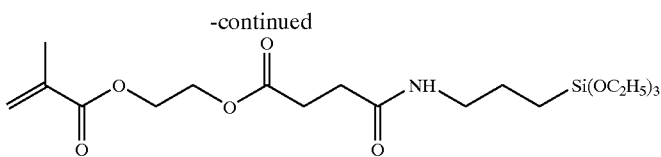

Suitable carboxylic acid methacrylates can be obtained by reacting di- or tetracarboxylic acid mono or dianhydrides with suitable OH-functionalized compounds capable of polymerization such as for example 2-hydroxyethylmethacrylate or glycerine dimethacrylate.

To synthesize silanes in which Y is equal to —(C=O)—NH—, the synthesis methods known in peptide chemistry, such as e.g. the DCC method or the mixed anhydrides method, can moreover also be used to react carboxylic acids with amino-group containing compounds, for example the reaction of an aminosilane with a carboxylic acid which contains p radicals W capable of polymerization:

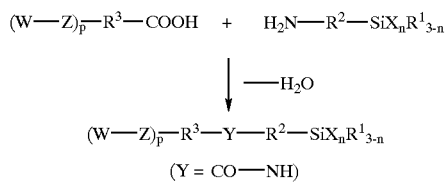

Thus, the reaction of 3-aminopropyltriethoxysilane with 2-methacryloyloxyethyl-hydrogen-succinate also results in 2-methacryloxyethyl-3-[(3-triethoxysilyl) propylaminocarbonyl]propionate:

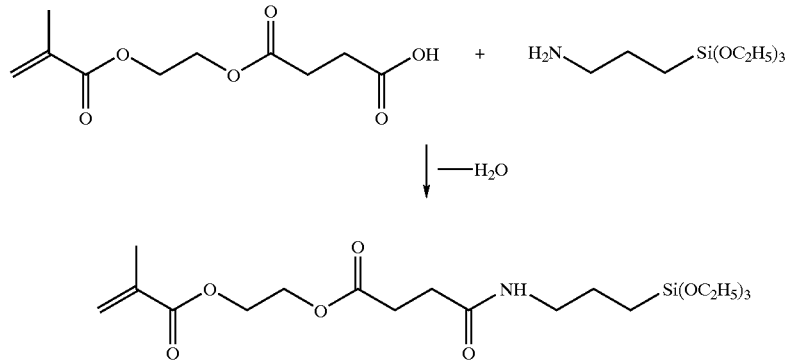

The silanes (I) are stable compounds and can be processed to give the polysiloxanes, either alone or together with other hydrolytically condensable compounds of silicon, aluminium, zirconium, titanium, boron, tin, vanadium and/or phosphorus. These additional compounds can be used either as such or already in pre-condensed form.

Preferred further hydrolytically condensable compounds of silicon are silanes of the general formula (II)

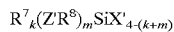  Formula (II)

in which

| | |
|---|---|
| $R^7$ | stands for a $C_1$ to $C_8$ alkyl, $C_2$ to $C_{12}$ alkenyl- or $C_6$ to $C_{14}$ aryl group; |
| $R^8$ | stands for a $C_1$ to $C_8$ alkylene, $C_2$ to $C_{12}$ alkenylene or $C_6$ to $C_{14}$ arylene group; |
| X' | stands for a hydrogen or halogen atom or a $C_1$ to $C_8$ alkoxy group; |
| Z' | stands for a glycidyl, acryl, methacryl, vinyl, allyl or vinyl ether group; |
| k | is equal to 0, 1, 2 or 3; |
| m | is equal to 0, 1, 2 or 3; and |
| k + m | is equal to 0, 1, 2 or 3. |

Preferred definitions, which can be chosen independently from each other, for the individual variables, are:

| | | |
|---|---|---|
| $R^7$ | = | a $C_1$ to $C_3$ alkyl, $C_2$ to $C_5$ alkenyl or a phenyl group; |
| $R^8$ | = | a $C_1$ to $C_5$ alkylene, $C_2$ to $C_5$ alkenylene or a phenylene group; |
| X' | = | a halogen atom, a methoxy or ethoxy group; |
| Z' | = | an acryl or methacryl group; |
| k | = | 0 and 1; |
| m | = | 0 and 1; |
| k + m | = | 0, 1 or 2. |

Such silanes are described for example in De 34 07 087 A1. Particularly preferred silanes of formula (II) are: $CH_3$—$SiCl_3$, $CH_3$—$Si(OC_2H_5)_3$, $C_2H_5$—$SiCl_3$, $C_2H_5$—$Si(OC_2H_5)_3$, $CH_2$=CH—$Si(OC_2H_5)_3$, $CH_2$=CH—$Si(OCH_3)_3$, $CH_2$=CH—$Si(OC_2H_4OCH_3)_3$, $(CH_3)_2SiCl_2$, $(CH_3)_2Si(OC_2H_5)_2$, $(C_2H_5)_3Si$—Cl, $(C_2H_5)_2Si(OC_2H_5)_2$, $(CH_3)_3Si$—Cl, $(CH_3O)_3Si$—$C_3H_6NH_2$, $(CH_3O)_3Si$—$C_3H_6SH_2$,

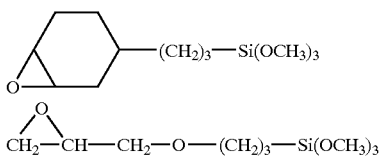

Silanes of the general formula (II) or pre-condensed products derived from them are preferably used in a quantity of 0 to 90 mol-%, particularly preferably 1 to 60 mol-% and quite particularly preferably 1 to 40 mol-% relative to the total mass of silanes of formulae (I) and (II) or pre-condensed products derived from them.

Preferred zirconium and titanium compounds are those according to formula (III)

$$MeX''_y R^9_z \quad \text{Formula (III)}$$

in which

| | | |
|---|---|---|
| Me | stands for | Zr or Ti; |
| $R^9$ | stands for | a hydrogen atom, a substituted or unsubstituted $C_1$ to $C_{12}$ alkyl, $C_1$ to $C_{15}$ alkylaryl or $C_6$ to $C_{14}$ aryl group; |
| X'' | stands for | a halogen atom, a hydroxyl or $C_1$ to $C_8$ alkoxy group; |
| Y | is equal to | 1 to 4; |
| Z | is equal to | 0 to 3. |

Preferred definitions, which can be chosen independently from each other, for the individual variables, are:

| | | |
|---|---|---|
| $R^9$ | = | a $C_1$ to $C_5$ alkyl or a phenyl group; |
| X'' | = | a halogen atom, a methoxy, ethoxy or propoxy group; |
| Y | = | 4; |
| Z | = | 0 or 1, in particular 0. |

Particularly preferred zirconium and titanium compounds are $ZrCl_4$, $Zr(OC_2H_5)_4$, $Zr(OC_3H_7)_4$, $Zr(OC_4H_9)_4$, $ZrOCl_2$, $TiCl_4$, $Ti(OC_2H_5)_4$, $Ti(OC_3H_7)_4$ and $Ti(OC_4H_9)_4$.

The zirconium and titanium compounds of the general formula (III) or pre-condensed products derived from them are preferably used in a quantity of 0 to 70 mol-%, particularly preferably 0 to 50 mol-% or 0 to 30 mol-% and quite particularly preferably 0 to 20 mol-% relative to the total mass of compounds of formulae (I) and (III) or pre-condensed products derived from them.

Preferred aluminium compounds are those according to formula (IV)

$$AlR^{10}_3 \quad \text{Formula (IV)}$$

in which $R^{10}$ stands for a halogen atom, a hydroxyl or $C_1$ to $C_8$-alkoxy group, preferably for a halogen atom or a $C_1$ to $C_5$-alkoxy group.

Particularly preferred aluminium compounds are $Al(OCH_3)_3$, $Al(OC_2H_5)_3$, $Al(OC_3H_7)_3$, $Al(OC_4H_9)_3$ and $AlCl_3$.

The aluminium compounds of the general formula (IV) or pre-condensed products derived from them are preferably used in a quantity of 0 to 70 mol-%, particularly preferably 0 to 30 mol-% and quite particularly preferably 0 to 20 mol-% relative to the total mass of compounds of formulae (I) and (IV) or pre-condensed products derived from them.

In addition, complexed compounds of zirconium, titanium and aluminium can be used, acids and β-dicarbonyl compounds being preferred as complexing agents. Preferred acids are acrylic and methacrylic acids or other methacrylate carboxylic acids such as e.g. 2-methacryloyloxyethyl hydrogen succinate or the 1:1-adducts of glycerine dimethacrylate and carboxylic acid anhydrides, such as e.g. succinic acid or phthalic anhydride. Preferred β-dicarbonyl compounds are acetylacetone, acetoacetic acid ethyl ester and in particular 2-acetoacetoxyethyl methacrylate. These complexing agents are preferably reacted with alkoxy derivates of zirconium, titanium or aluminium in the molar ratio of 1:1.

In addition, boron trihalides, stannic tetrahalides, stannic tetraalkoxides and/or vanadyl compounds are suitable for co-condensation with the silanes according to formula (I).

When using additional hydrolytically condensable compounds, the proportion of silanes according to formula (I) in the polysiloxanes is preferably 10 to 99 mol-%, particularly preferably 40 to 99 mol-%, each relative to the initial monomer compounds. The proportion of silanes (I) and (II) together is preferably at least 20 mol-%, particularly preferably at least 80 mol-%, likewise relative to the initial monomer compounds.

The manufacture of the polysiloxanes is carried out by hydrolytic condensation of the above-listed compounds. In the case of the silanes of the general formulae (I) and (II), the hydrolyzable groups X are first split off, silanoles, silane diols and silane triols being obtained which condense to polysiloxanes with an inorganic network of Si—O—Si units accompanied by splitting-off of water.

The hydrolytic condensation of the silanes generally takes place by reacting the silicon compound to be hydrolized, either directly or dissolved in a suitable solvent, at room temperature or accompanied by slight cooling, at least with the quantity of water stoichiometrically required for complete hydrolysis and stirring the resulting mixture for one or several hours. Aliphatic alcohols such as for example ethanol or isopropanol, dialkyl ketones such as acetone or methylisobutyl ketone, ethers such as for example diethyl ether or tetrahydrofuran (THF), esters such as for example ethyl or butyl acetate and mixtures thereof are in particular suitable as solvents.

The hydrolysis and condensation of the initial mixture preferably takes place in the presence of a condensation catalyst, with compounds splitting off protons or hydroxyl ions, such as organic or inorganic acids or bases, and also compounds releasing fluoride ions, such as ammonium fluoride or sodium fluoride, being preferred. Particularly preferred are volatile acids or bases, in particular hydrochloric acid or ammonia. During the hydrolysis and condensation, it has proved worthwhile to adopt sol-gel techniques, as described for example in C. J. Brinker et al., "Sol-Gel-Science", Academic Press, Boston, 1990.

If the hydrolytic condensation is carried out in the presence of zirconium, titanium or aluminium compounds, the water is preferably added stepwise, the temperature preferably being kept in the range of approximately 0 to 30° C. It is often advantageous to add water in the form of hydrous solvents such as for example aqueous ethanol, or to produce it in situ, for example by chemical reactions such as esterifications.

The polysiloxanes obtained can be used directly or after partial or complete removal of the solvent. It is often advantageous to replace the solvent used for the hydrolytic condensation with another solvent. The silanes (I) and in particular the polysiloxanes show only a low volatility because of their high molecular weight and therefore can largely be processed safely. With regard to the mechanical properties of the polysiloxanes, it is advantageous to perform the hydrolytic condensation up to a degree condensation of 65 to 95 mol-%, the degree of condensation being able to be measured by $^{29}$Si-NMR.

The complete curing of the polysiloxanes takes place by the addition of suitable initiators and optionally further components capable of polymerization by thermal, photochemical or redox-induced polymerization. Several curing mechanisms, e.g. radical and cationic polmerization, can also be used simultaneously or in successive steps when different groups capable of polymerization, e.g. (meth)acryl and epoxide groups, are present.

To initiate the radical polymerization, thermal and/or photoinitiators are preferably used.

Preferred initiators for the thermal curing are peroxides such as for example dibenzoyl peroxide, dilauryl peroxide, tert.-butylperoctoate and tert.-butylperbenzoate as well as azobisisobutyroethyl ester, benzpinacol and 2,2-dimethylbenzpinacol.

Preferred photoinitiators are benzophenone and benzoin as well as their derivatives, α-diketones and their derivatives such as for example 9,10-phenanthrenequinone, diacetyl and 4,4-dichlorobenzil. Particularly preferred photoinitiators are camphorquinone and 2,2-methoxy-2-phenyl-acetophenone and in particular combinations of α-diketones with amines as reducing agents such as for example N-cyanoethyl-N-methylaniline, 4-(N,N-dimethylamino)-benzoic acid ester, N,N-dimethylaminoethyl methacrylate, N,N-dimethyl-sym.-xylidine or triethanolamine. In addition, acylphosphines such as for example 2,4,6-trimethylbenzoyldiphenyl or bis-(2,6-dichlorobenzoyl)-4-N-propylphenyl phosphinic oxide, are suitable as photoinitiators.

Diaryliodonium or triarylsulfonium salts such as for example triphenylsulfoniumhexafluorophosphate and triphenylsulfoniumhexafluoroantimoniate are particularly suitable for the dual curing of radically and cationically polymerizable systems.

Redox initiator combinations such as for example combinations of benzoyl or lauryl peroxide with N,N-dimethyl-sym.-xylidine or N,N-dimethyl-p-toluidine are used as initiators for a polymerization at room temperature.

The polymerization of polysiloxanes with 2 or more (meth)acrylate radicals results in three-dimensional organic networks, in which the mechanical properties such as for example strength and flexibility, as well as the physico-chemical properties of the cured materials such as for example adhesivity, water absorption and refractive index, can be varied via the distance between the Si atoms and the (meth)acrylate radicals capable of polymerization, i.e. via the length of the spacer group —R$^2$—Y—R$^3$—Z—R$^6$—, as well as via the presence of further functional groups, and optimally matched to the requirements of each application case. The use of aliphatic groups as spacers results in relatively flexible, and the use of aromatic groups relatively rigid products.

The crosslinking density of the cured materials can be set by the number of (meth)acrylate groups capable of polymerization, which allows a further influencing of the properties and possible uses of the polysiloxanes.

If the monomeric silanes contain, in addition, ionically crosslinkable groups such as for example epoxide or oxethane groups, a further increase in the crosslinking density can be achieved by their simultaneous or subsequent ionic polymerization.

The polysiloxanes can be used mixed with suitable ionically and/or radically polymerizable mono- or multifunctional monomers. Preferred monomers are mono(meth) acrylates, such as methyl, ethyl, butyl, benzyl, furfuryl or phenyl (meth)acrylate, multifunctional acrylates and methacrylates such as for example bisphenol-(A)-di(meth) acrylate, bis-GMA (an addition product of methacrylic acid and bisphenol-A-diglycidyl ether), UDMA (an addition product of 2-hydroxyethyl methacrylate and 2,2,4-hexamethylene diisocyanate), di-, tri- and tetraethylene glycol-di(meth)acrylate, decanedioldi(meth)acrylate, trimethylol propane tri(meth)acrylate, pentaerythritol tetra (meth)acrylate and butane diol-di(meth)acrylate, 1,10-decanediol-di(meth)acrylate or 1,12-dodecanediol-di(meth) acrylate.

The polymerizable monomers are preferably used in a quantity of 1 to 80 wt-%, particularly preferably 5 to 50 wt-% and quite particularly preferably 5 to 30 wt-% relative to the total mass of polymerizable monomer and silanes of the formula (I) or pre-condensed products derived from them.

The mixtures can moreover contain further additives such as colorants (pigments and dyes), stabilizers, flavoring agents, microbiocidal active ingredients, plasticizers and/or UV absorbers.

Furthermore, to improve the mechanical properties, the compositions can be filled with organic or inorganic particles or fibres. Preferred inorganic particulate fillers are amorphous spherical materials based on mixed oxides of $SiO_2$, $ZrO_2$ and/or $TiO_2$ (DE 40 29 230 Al), microfine fillers such as pyrogenic silicic acid or precipitation silicic acid as well as macro- (particle size 5 µm to 200 µm) or minifillers (particle size 0.5 to 5 µm) such as quartz, glass ceramic or glass powders with an average particle size of 0.5 µm to 5 µm as well as X-ray opaque fillers such as ytterbium trifluoride. In addition, glass fibres, polyamide or carbon fibres can also be used as fillers.

The compositions are in particular suitable as dental materials such as adhesives, coating materials, dental cements and filling materials.

The dental materials according to the invention preferably contain (a) 5 to 99.9 wt-%, preferably 5 to 90 wt-%, particularly preferably 10 to 70 wt-% polysiloxane; and (b) 0.1 to 5.0 wt-%, preferably 0.2 to 2.0 wt-% polymerization initiator; and preferably (c) 1.0 to 80 wt-%, preferably 5.0 to 50 wt-% ionically and/or radically polymerizable monomer; and preferably (d) 1.0 to 90 wt-%, preferably 2.0 to 80 wt-% fillers.

The figures given are in each case relative to the total mass of the dental material.

In the following, the invention is explained in more detail with reference to embodiments.

EXAMPLE 1

Synthesis of bis[2-(2-methacryloyloxyethoxycarbonyl)-ethyl]-(3-triethoxysilylpropyl)amine

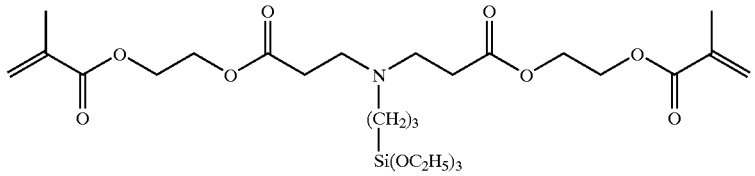

43 g (0.25 mol) 3-aminopropyl triethoxysilane in 40 ml anhydrous acetonitrile are added dropwise accompanied by ice-cooling to 92 g (0.5 mol) 2-acryloyloxyethyl methacrylate in 85 ml acetonitrile. After 48 h stirring at room temperature, the aminosilane has completely reacted. The solvent is evaporated off accompanied by the introduction of air at reduced pressure at the rotary evaporator at maximally 46° C. 132.2 g (98% yield) of a lightly-coloured clear oily liquid are obtained.

$^1$H-NMR (400 MHz, CDCl$_3$): δ=0.58 (t, 2H, SiCH$_2$), 1.22 (t, 9H, CH$_3$), 1.52 (m, 2H, CH$_2$), 1.95 (s, 3H, CH$_3$=C), 2.45 (m, 6H, NCH$_2$), 2.78 (t, 4H, O=C—CH$_2$), 3.82 (q, 6H, OC$\underline{H}_2$CH$_3$), 4.34 (s, 8H, OCH$_2$CH$_2$O), 5.59 and 6.16 (2s, 4H, =CH$_2$) ppm.

IR (film): 2974 (s), 1724 (s), 1637 (w), 1320 (m), 1296 (m), 1163 (s) and 1078 (m) cm$^{-1}$.

EXAMPLE 2

Synthesis of the Adduct of 3-aminopropylsilane to 2(1)-acryloyloxy-1(2),3-dimethacryloyloxypropane 1$^{st}$ Step 2(1)-acryloyloxy-1(2),3-di(methacryloyloxy)propane 64 g (0.7 mol) acrylic acid chloride in 290 ml ether are added dropwise to an ice-cooled solution of 135 g (0.6 mol) glycerine dimethacrylate (GDMA) and 85 g (0.7 mol) collidine in 290 ml ether. After 16 h stirring at room temperature, the collidinium hydrochloride precipitate formed is filtered off and the ether solution washed twice with 100 ml 1N HCl each time, twice with 100 ml 10% sodium hydrogen carbonate solution each time and 3 times with 100 ml water each time. The ether phase is dried over anhydrous Na$_2$SO$_4$, stabilized with 20 mg hydroquinone monomethyl ether (MEHQ) and the solvent distilled off accompanied by introduction of air at the rotary evaporator at reduced pressure. 79 g (98% yield) of dark yellow, clear liquid are obtained.

$^1$H-NMR (400 MHz, CDCl$_3$): δ=1.94 (s, 6H, CH$_3$), 4.20–4.44 and 5.48 (m, 5H, CHO, CH$_2$O) and 5.60–6.78 (m, 7H, =CH$_2$, CH=CH$_2$) ppm.

A detailed comparison of the integral ratios shows that the reaction is complete and the product contains 13% GDMA.

IR (film): 2960 (m), 1728 (s), 1638 (s), 1407 (s), 1294 (s) and 1163 (s) cm$^{-1}$.

2$^{nd}$ Step Reaction of 3-aminopropylsilane with 2(1)-acryloyloxy-1(2),3-di(methacryloyloxy)propane

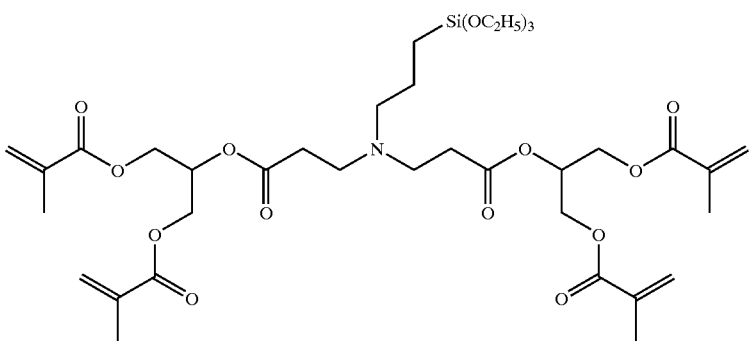

A solution of 63.3 g (224 mmol) 2(1)-acryloyloxy-1(2),3-dimethacryloyloxypropane, 24.8 g (111 mmol) 3-aminopropyltriethoxysilane, 50 mg MEHQ in 200 ml absolute methanol is stirred for 6 d under argon at 40° C. The methanol is removed on the rotary evaporator, accompanied by introduction of dry air, at 40° C. and at reduced pressure. 79 g (89% yield) of a dark yellow, clear liquid are obtained.

$^1$H-NMR (400 MHz, CDCl$_3$): δ=0.59 (t, 2H, SiCH$_2$), 1.25 (q, CH$_3$), 1.50–1.52 (m, 2H, CH$_2$), 1.96 (s, 12H, CH$_3$), 2.42–2.44 (m, 6H, NCH$_2$), 2.76 (t, 4H, O=C—CH$_2$), 3.56 (s, OCH$_3$), 3.80 (t, OCH$_2$), 4.19–4.40 and 5.18 (m, 10H, CHO and CH$_2$O) and 5.60 and 6.15 (2s, 8H, =CH$_2$) ppm.

The $^1$H-NMR-spectrum shows that an ester interchange partially took place with the solvent methanol at the triethoxysiyl group during the reaction.

IR (film): 3504 (w), 2954 (m), 1724 (s), 1637 (m), 1453 (m), 1296 (s) and 1162 (s) cm$^{-1}$.

Example 3

Synthesis of 2-methacryloyloxyethyl-3-[(3-triethoxysilyl)-propylaminocarbonyl]propionate 1$^{st}$ Step 2-methacryloyloxyethyl hydrogen succinate

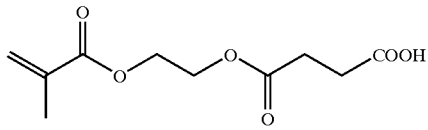

40 g (0.4 mol) succinic acid anhydride, 52 g (0.4 mol) HEMA and 80 mg MEHQ in 200 ml dioxane are mixed with 2 drops of conc. sulphuric acid and heated for 5 hours to 80° C. The dioxane is largely distilled off at the rotary evaporator with applied oil pump vacuum (1–5 mbar) accompanied by introduction of air. The product is then taken up in 100 ml methylene chloride and washed 3 times with 100 ml water each time and dried over anhydrous sodium sulphate. After renewed stabilizing with 40 mg MEHQ, the solvent is removed under reduced pressure and accompanied by introduction of air. 80 g (87% yield) of a yellow-coloured liquid are obtained.

$^1$H-NMR (400 MHz, CDCl$_3$): δ=1.93 (s, 3H, CH$_3$), 2.53–2.64 (m, 4H, C$\underline{H}_2$C$\underline{H}_2$COOH), 4.31 (s, 4H, OCH$_2$CH$_2$O), 5.61 and 6.11 (2s, 2H =CH$_2$) and 10.70 (br, 1H, COOH) ppm.

IR (film): 3400–2400 (br), 2960 (m), 1722 (s), 1698 (s), 1636 (m), 1406 (m) and 1147 (s) cm$^{-1}$.

2$^{nd}$ Step 2-methacryloyloxyethyl-3-[(3-triethoxysilyl)propyl-aminocarbonyl]-propionate

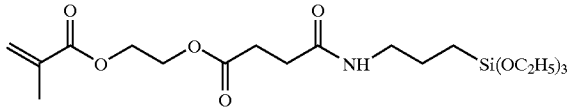

20 g (87 mmol) 2-methacryloyloxyethyl hydrogen succinate, 21.5 g (87 mmol) 3-isocyanatopropyl triethoxysilane and 2 drops of dibutyl tin dioctoate are stirred at room temperature in 50 ml methylene chloride until no more isocyanate can be detected in the IR spectrum (approx. 3 days). The reaction solution is stabilized with 30 mg MEHQ and the solvent distilled off with introduction of dry air at the rotary evaporator. 33.7 g (90% yield) of a coloured liquid are obtained.

$^1$H-NMR (400 MHz, CDCl$_3$): δ=0.65 (t, 2H, CH$_2$Si), 1.23 (t, 9H, CH$_3$), 1.61–1.62 (m, 2H, CH$_2$), 1.95 (s, 3H, CH$_3$), 2.51–2.67 (m, 4H, CH$_2$CH$_2$CO$_2$), 3.10–3.20 (m, 2H, CH$_2$N), 3.81 (q, 6H, CH$_2$O), 4.27 (br, 1H, NH), 4.37 (s, 4H, OCH$_2$CH$_2$O) and 5.45 and 6.14 (2s, 2H, =CH$_2$) ppm.

IR (film): 3346 (w), 2975 (m), 1724 (s), 1639 (w), 1297 (m) and 1159 (s) cm$^{-1}$.

EXAMPLE 4

Hydrolytic Condensation of bis (methacryloylethoxycarbonylethyl)-[3-(triethoxysilylpropyl)]amine 100 mmol of the silane from example 1 are dissolved in 30 ml anhydrous ethanol. The pre-hydrolysis of the silane is carried out by adding 300 mmol of water in the form of a 0.1 N NH$_4$F solution. After 16 to 20 h stirring at room temperature, the volatile components are removed under vacuum and a low-viscosity resin (η=1.6 Pas) is formed which, after the addition of a radical initiator, can be used as a component for a light-curing coating or a light-curing dental material.

EXAMPLE 5

Hydrolytic Condensation of bis (methacryloylethoxycarbonylethyl)-[3-(triethoxysilylpropyl)]amine and subsequent silylation 100 mmol of the silane from example 1 are dissolved in 250 ml EtOH. The hydrolysis of the silane is carried out by the addition of 300 mmol of water in the form of a 0.1 N NH$_4$F solution. After 16 to 22 h stirring at room temperature, the volatile components are removed under vacuum. The viscous resin formed is dissolved in 80 ml THF and, for silylation of still-present Si—OH groups mixed accompanied by cooling with 100 mmol collidine as a base and 100 mmol trimethylchlorosilane (TMCS). To complete the reaction, the mixture is stirred for 12 to 24 h at room temperature before the precipitate formed is filtered off. After the removal of the volatile components under vacuum, a low-viscosity resin (η=4.9 Pas (23° C.)) is obtained which, after the addition of a radical initiator, can be used as such or as a component for a light-curing coating or a light-curing dental material.

To measure the mechanical properties, corresponding testpieces were produced from the resin and cured by illumination (6 minutes) with a Spectramat dental radiation source (Vivadent). The polymerization shrinkage (ΔV) was calculated from the difference of the resin and polymer density measured by gas pycnometry and the flexural strength (FS) or the flexural-E-moduus (FEM) measured according to ISO standard 4049 (1988), each testpiece being dried at 37° C. for 24 h. The results are: FS=67 MPa, FEM=1950 MPa, ΔV=−7.3 vol-%. A glass transition temperature of the polymerisate of T$_G$=95° C. was measured by means of a dynamic-mechanical analysis.

EXAMPLE 6

Hydrolytic Condensation of the Adduct of 3-aminopropylsilane with 2(1)-acryloyloxy-1(2),3-di(methacryloyloxy)propane 100 mmol of the silane from example 2 are dissolved in 300 ml anhydrous ethanol. The pre-hydrolysis of the silane was carried out by adding 150 mmol water in the form of a 0.1 N NH$_4$F solution. After 16 to 20 h of stirring at room temperature, the volatile components are removed under vacuum and a low-viscosity resin (η=2.8 Pas) is obtained which, after the addition of a radical initiator, can be used as a component for a light-curing coating or a light-curing dental material.

EXAMPLE 7

Preparation of a Dental Cement

A dental cement of the following formulation is prepared on the basis of the resin from example 5 obtained after hydrolytic condensation and subsequent silylation:

| Resin from example 5: | 31.6 wt-% |
|---|---|
| UDMA: | 7.8 wt-% |
| Silanized OX-50: | 41.4 wt-% |
| YbF$_3$: | 18.7 wt-% |
| Photoinitiator*) | 0.5 wt-% |

OX-50 = silanized pyrogenic silicic acid (Degussa), primary particle size 40 nm
YbF3 = ytterbium fluoride (Rhone-Poulenc)
*)mixture of equal proportions of camphorquinone and N-(2-cyanoethyl)-N-methylaniline The components are processed to a paste with an Exakt-type triple roll mill (Exakt Apparatebau) and testpieces are then manufactured and tested analogously to example 5. The results are: FS=62 MPa, FEM=3260 MPa and ΔV=−3.6 vol-%.

What is claimed is:

1. A dental material, comprising a polysiloxane which comprises an inorganic network of Si—O—Si units prepared from the condensation reaction of a plurality of monomeric silanes according to Formula (I)

$$[(W_q\text{---}R^6\text{---}Z)_p\text{---}R^3]_m Y\text{---}R^2\text{---}SiX_n R^1{}_{3-n}\quad \text{Formula (I)}$$

in which

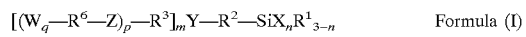

| X | stands for a halogen atom, a hydroxyl, alkoxy and/or acyloxy group; |
|---|---|
| n | is equal to 1 to 3; |
| R$^1$ | stands for an alkyl, alkenyl, aryl, alkylaryl, arylalkyl group; |
| R$^2$ | stands for an alkylene group; |
| R$^3$ | stands for a p-times substituted, straight, branched or cyclic, saturated or unsaturated, aromatic or aliphatic organic radical with 2 to 40 carbon atoms and optionally 1 to 6 heteroatoms; |
| R$^6$ | stands for a q-times substituted, straight, branched or cyclic organic radical with 1 to 20 carbon atoms, or is absent; |
| p | is equal to 1 to 6; |
| q | is equal to 1 to 6; |
| Y | stands for —NR$^4$—, N or —(C═O)—NH—; |
| m | is equal to 2 for Y = N and equal to 1 for Y = —NR$^4$— or —(C═O)—NH—; |
| R$^4$ | stands for an alkyl or aryl group; |
| Z | stands for O, S, —(C═O)—O—, —(C═O)—NH—, —O—(C═O)—NH— or is absent; |
| W | stands for CH$_2$═CR$^5$—(C═O)—O—; |
| R$^5$ | stands for hydrogen atom or an alkyl group and optionally one or several hydrolytically condensable compounds of silicon, aluminium, zirconium, titanium, boron, tin, vanadium and/or phosphorus. |

2. A dental material according to claim 1, wherein

| X | stands for a methoxy and/or ethoxy group; |
|---|---|
| n | is 2 or 3; |
| R$^1$ | stands for a C$_1$ to C$_3$ alkyl group; |
| R$^2$ | stands for a C$_1$ to C$_4$ alkylene group; |

| R$^3$ | stands for a p-times substituted, straight, branched or cyclic, saturated or unsaturated, aromatic or aliphatic organic radical with 2 to 10 carbon atoms and optionally a heteroatom; |
|---|---|
| R$^6$ | stands for a q-times substituted, straight, branched or cyclic organic radical with 1 to 4 carbon atoms; |
| p | is equal to 1 or 2; |
| q | is equal to 1 or 2; |
| Y | stands for N or —(C═O)—NH—; |
| Z | for —(C═O)—O—; |
| R$^5$ | stands for hydrogen atom or a methyl group. |

3. A dental material according to claim 1, wherein the hydrolytically condensable compound is a silane according to Formula (II)

$$R^7{}_k(Z'R^8)_m SiX'_{4-(k+m)}\quad \text{Formula (II)}$$

in which

| R$^7$ | stands for a C$_1$ to C$_8$ alkyl, C$_2$ to C$_{12}$ alkenyl or C$_6$ to C$_{14}$ aryl group; |
|---|---|
| R$^8$ | stands for a C$_1$ to C$_8$ alkylene, C$_2$ to C$_{12}$ alkenylene or C$_6$ to C$_{14}$ arylene group; |
| X' | stands for a hydrogen or halogen atom or a C$_1$ to C$_8$ alkoxy group; |
| Z' | stands for a glycidyl, acryl, methacryl, vinyl, allyl or vinyl ether group; |
| k | is equal to 0, 1, 2, or 3; |
| m | is equal to 0, 1, 2, or 3; and |
| k + m | is equal to 0, 1, 2, or 3; | a zirconium and/or titanium compound of Formula (III)

$$MeX''_y R^9{}_z\quad \text{Formula (III)}$$

in which

| Me | stands for Zr or Ti; |
|---|---|
| R$^9$ | stands for a hydrogen atom, a substituted or unsubstituted C$_1$ to C$_{12}$ alkyl, C$_1$ to C$_{15}$ alkyl aryl or C$_6$ to C$_{14}$ aryl group; |
| X'' | stands for a halogen atom, a hydroxyl or C$_1$ to C$_8$ alkoxy group; |
| y | is equal to 1 to 4; and |
| z | is equal to 0 to 3; | an aluminum compound according to the Formula IV $$AlR^{10}{}_3\quad \text{Formula (IV)}$$

in which

R$^{10}$ stands for a halogen atom, a hydroxyl or C$_1$ to C$_8$ alkoxy group;

and/or a boron trihalide, stannic tetrahalide, stannic tetraalkoxide and/or a vanadyl compound.

4. A dental material according to claim 3, wherein

| R$^7$ | = is a C$_1$ to C$_3$ alkyl, C$_2$ to C$_5$ alkenyl or a phenyl group; |
|---|---|
| R$^8$ | = is a C$_1$ to C$_5$ alkylene, C$_2$ to C$_5$ alkenylene or a phenylene group; |
| X' | = is a halogen atom, a methoxy or ethoxy group; |
| Z' | = is an acryl or methacryl group; |
| k | = 0 or 1; |
| m | = 0 or 1; |

-continued

| | | |
|---|---|---|
| k + m and/or | = | 0, 1 or 2; |
| $R^9$ | = | is a $C_1$ to $C_5$ alkyl or a phenyl group; |
| X" | = | is a halogen atom, a methoxy, ethoxy or propoxy group; |
| y | = | is 4; |
| z and/or | = | 0 or 1; |
| $R^{10}$ | = | a halogen atom or a $C_1$ to $C_5$ alkoxy group. |

5. A dental material according to claim 3, wherein
the silane or silanes according to the general Formula (II) or pre-condensed products derived therefrom are in a quantity of 1 to 90 mol-%; and, or
the zirconium and/or titanium compound of the general Formula (III) or pre-condensed products derived therefrom are in a quantity of 0 to 70 mol-%; and/or
the aluminum compound of the general Formula (IV) or pre-condensed products derived from it are in a quantity of 0 to 70 mol-%,
relative to the total mass of compounds of the Formula (I) and/or pre-condensed products derived therefrom and compounds of Formula (II), Formula (III) or Formula (IV).

6. A dental material according to claim 1, wherein the polysiloxane contains 10 to 99 mol-% of a silane according to Formula (I), relative to the initial monomer compounds.

7. A dental material according to claim 1 further comprising:
an ionically and/or radically polymerizable monomer.

8. A dental material according to claim 7, further comprising:
a methyl, ethyl, butyl, benzyl, furfuryl and/or phenyl (meth)acrylate, bisphenol-A-di(meth)-acrylate, Bis-GMA, UDMA, di-, tri-, or tetraethylene-glycol di(meth)acrylate, decanediol(meth)acrylate, trimethylolpropane tri(meth)acrylate, pentaerythritol tetra (meth)acrylate, butanediol di(meth)acrylate, 1,10-decanediol di(meth)acrylate or 1,12-dodecanediol di(meth)acrylate or a mixture of these monomers.

9. A dental material according to claim 1 further comprising:
a filler.

10. A dental material according to claim 1 further comprising:
an initiator for radical polymerization.

11. A dental material according to claim 1 comprising:
(a) 5 to 99.9 wt-% polysiloxane; and
(b) 0.1 to 5.0 wt-% polymerization initiator.

12. A dental material according to claim 1, wherein the dental material is a composite material, a cement, a filling material, or a bonding.

13. A dental material according to claim 11, wherein the dental material further comprises:
(c) 1.0 to 80 wt-% ionically and/or radically polymerizable monomer; and
(d) 1.0 to 90 wt-% filler.

* * * * *